US011395664B1

(12) United States Patent
Ju et al.

(10) Patent No.: US 11,395,664 B1
(45) Date of Patent: Jul. 26, 2022

(54) POWER TOOL FOR ORTHOPEDIC SURGERY

(71) Applicant: IMEDICOM CO., LTD., Gunpo-si (KR)

(72) Inventors: Don Soo Ju, Gunpo-si (KR); Byoung Ju Lee, Gunpo-si (KR); Seung Hyeok Noh, Gunpo-si (KR)

(73) Assignee: IMEDICOM CO., LTD., Gunpo-si (KR)

( * ) Notice: Subject to any disclaimer, the term of this patent is extended or adjusted under 35 U.S.C. 154(b) by 0 days.

(21) Appl. No.: 17/403,290

(22) Filed: Aug. 16, 2021

(30) Foreign Application Priority Data

Mar. 4, 2021 (KR) .......................... 10-2021-0028656

(51) Int. Cl.
*A61B 17/16* (2006.01)
(52) U.S. Cl.
CPC ...... *A61B 17/1626* (2013.01); *A61B 17/1628* (2013.01)
(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628
See application file for complete search history.

(56) References Cited

U.S. PATENT DOCUMENTS

| | | | | |
|---|---|---|---|---|
| 8,029,510 | B2* | 10/2011 | Hoegerle | A61B 17/1628 388/907 |
| 9,295,476 | B2* | 3/2016 | Hassler, Jr. | H03K 17/97 |
| 9,924,954 | B2* | 3/2018 | Guo | A61B 17/14 |
| 10,159,495 | B1* | 12/2018 | Lambert | A61B 17/1615 |
| 10,390,869 | B2* | 8/2019 | McGinley | A61B 17/8872 |
| 10,695,074 | B2* | 6/2020 | Carusillo | A61B 17/1626 |
| 10,751,104 | B2* | 8/2020 | Mistry | A61B 17/32 |
| 10,758,250 | B2* | 9/2020 | McGinley | A61B 17/15 |
| 11,253,330 | B2* | 2/2022 | Flatt | A61B 17/162 |
| 2008/0077149 | A1* | 3/2008 | Hoegerle | A61B 17/1613 606/178 |

(Continued)

FOREIGN PATENT DOCUMENTS

EP 2675370 B1 11/2017
JP 2019184404 A 10/2019
KR 101515529 B1 4/2015

*Primary Examiner* — Eric S Gibson
(74) *Attorney, Agent, or Firm* — Rabin & Berdo, P.C.

(57) ABSTRACT

A power tool for orthopedic surgery is provided, which can be coupled with an attachment having one or more first magnets mounted thereon, and include a power tool body including a power tool case, an attachment fastening portion connected to one end of the power tool body, a motor power transmitting portion protruding toward the attachment fastening portion and transmitting power to the attachment, a motor that drives the motor power transmitting portion, a first magnetic sensor portion including a first magnetic sensor capable of sensing a magnetic field strength or number of the one or more first magnets, a control portion that controls the motor to operate below a preset maximum rotational speed and maximum torque value according to the magnetic field strength or the number sensed by the first magnetic sensor, and a power supply that supplies power to the motor and the control portion.

9 Claims, 13 Drawing Sheets

(56) References Cited

U.S. PATENT DOCUMENTS

| | | | | |
|---|---|---|---|---|
| 2013/0289565 | A1* | 10/2013 | Hassler, Jr. | A61B 18/00 606/79 |
| 2015/0245846 | A1* | 9/2015 | Guo | A61B 17/14 606/82 |
| 2015/0313612 | A1* | 11/2015 | Edwards | B23B 31/005 606/80 |
| 2016/0128704 | A1* | 5/2016 | McGinley | A61B 17/1637 606/86 R |
| 2017/0224400 | A1* | 8/2017 | Mistry | A61B 18/00 |
| 2018/0250020 | A1* | 9/2018 | Carusillo | A61B 17/1615 |
| 2020/0093555 | A1* | 3/2020 | Flatt | A61B 34/30 |
| 2020/0323543 | A1* | 10/2020 | Carusillo | A61B 17/1633 |
| 2020/0352619 | A1* | 11/2020 | Mistry | A61B 17/1659 |
| 2021/0052285 | A1* | 2/2021 | Carusillo | A61B 17/1626 |
| 2021/0085343 | A1* | 3/2021 | McGinley | A61B 17/17 |
| 2021/0186524 | A1* | 6/2021 | Carusillo | A61B 17/162 |
| 2021/0378684 | A1* | 12/2021 | Lambert | A61B 17/1622 |

* cited by examiner

POWER TOOL FOR ORTHOPEDIC SURGERY

CROSS-REFERENCE TO RELATED APPLICATIONS

This application claims priority from Korean Patent Application No. 10-2021-0028656, filed on Mar. 4, 2021 in the Korean Intellectual Property Office, the disclosure of which is incorporated herein by reference in its entirety.

BACKGROUND

Technical Field

The present disclosure relates to a power tool for orthopedic surgery, and more particularly, to a power tool for orthopedic surgery that can be coupled with various attachments and can identify the attachments coupled therewith so as to control a maximum rotational speed and a maximum torque value of a motor.

Background Art

For drilling, trimming, cutting, implanting screws for bone fusion, or the like, attachments suitable for each function are fastened to a surgical power tool and used, and in general, drilling a bone requires a rotational speed of 1,000 to 12,000 RPM of the power tool and a torque of 15 N cm, trimming a bone requires a rotational speed of 300-350 RPM and a torque of 100 N cm, and cutting a bone requires 10,000 to 20,000 RPM. In addition, the implantation of a screw for bone fusion requires, depending on a diameter of the screw, a rotational speed of 100 RPM or less and a torque value of 25 to 45 N cm.

However, the related power tool for orthopedic surgery has a fixed maximum rotational speed and maximum torque value, and the attachment has a fixed gear ratio, and with this fixed gear ratio, in general, there is a limit to the gear ratio that can be set for each function required for each surgery because the attachments use the same gear module.

For example, when the rotational speed of the power tool for orthopedic surgery is 3,600 RPM, and the gear ratio of the first stage of the reduction gear of the attachment is 1:3, the attachment for drilling using the first gear is fixed at 1,200 RPM, the attachment for trimming using the second gear is fixed at 400 RPM, and the attachment for implanting a screw using the third gear is fixed at 133 RPM. In this case, in general, the rotational speed exceeds the speed required for each operation, and the torque value is gradually increased.

In this case, there is a problem of risks and inconveniences that can occur, such as bone necrosis due to high heat from the fast rotational speed during surgery such as drilling, trimming, cutting, implantation, and the like, damages to the screw due to high torque during screw implantation, and the like.

SUMMARY

The present disclosure has been made to solve the problems mentioned above, and it is an object of the present disclosure to provide a power tool for orthopedic surgery which can be coupled with an attachment for each function and identify the attachment coupled therewith so as to control a motor to stay within a preset maximum rotational speed and maximum torque value, thereby improving related problems that may occur during orthopedic surgery.

In order to achieve the object described above, a power tool for orthopedic surgery according to an embodiment may be coupled with an attachment having one or more first magnets mounted thereon, and include a power tool body having a power tool case, an attachment fastening portion connected to one end of the power tool body, a motor power transmitting portion protruding toward the attachment fastening portion and transmitting power to the attachment, a motor that drives the motor power transmitting portion, a first magnetic sensor portion including a first magnetic sensor capable of sensing a magnetic field strength or number of the one or more first magnets, a control portion that controls the motor to operate below a preset maximum rotational speed and maximum torque value according to the magnetic field strength or the number sensed by the first magnetic sensor, and a power supply that supplies power to the motor and the control portion.

In addition, the attachment fastening portion may include a receiving portion for receiving the attachment, the first magnetic sensor portion may be disposed between an outer wall of the receiving portion and the power tool case, and the receiving portion may include a non-magnetic portion formed in a sensing direction of the first magnetic sensor.

In addition, the attachment may include an attachment body to be received in the receiving portion, and a power transmission fastening portion disposed inside the attachment body and rotatable relative to the attachment body while interlocking with the motor power transmitting portion, and the one or more first magnets may be provided on the attachment body in a circumferential direction, and disposed to face the first magnetic sensor while the non-magnetic portion of the receiving portion is interposed between itself and the first magnetic sensor.

In addition, the first magnetic sensor portion may be electrically connected to the control portion.

In addition, the attachment fastening portion may further include a sliding portion slidable relative to the receiving portion, the sliding portion may include a sliding portion distal end and a sliding portion proximal end having an inner diameter smaller than the sliding portion distal end, and the receiving portion may include an inner member receiving the attachment therein and including an inner member distal end and an inner member proximal end having an outer diameter smaller than the inner member distal end, an outer member forming an annular groove in cooperation with the inner member proximal end, a first elastic member disposed in the annular groove in a compressed state, with one end disposed in contact with the sliding portion, and a plurality of fastening balls respectively disposed in a plurality of through holes in a wall thickness direction of the inner member and movable in the wall thickness direction of the inner member.

In addition, the attachment body may include a plurality of fastening ball grooves at positions corresponding to the positions of the plurality of fastening balls, and when the attachment body is completely received in the inner member such that the power transmission fastening portion is coupled with the motor power transmitting portion, a portion of the fastening ball may be inserted into the fastening ball groove such that the attachment body may be fixed to the inner member, and when the sliding portion is slid from the inner member distal end toward the inner member proximal end while overcoming a restoring force of the first elastic member, the fastening balls may be separated from the fastening ball grooves while moving toward the sliding portion distal end such that the attachment body may be released from being fixed to the inner member.

In addition, when one first magnet is mounted on the attachment, according to a magnetic field strength sensed by the first magnetic sensor, the control portion may control the motor to operate below the preset maximum rotational speed and maximum torque value, and when two or more first magnets are mounted on the attachment, according to the number of the first magnets sensed by the first magnetic sensor, the control portion may control the motor to operate below the preset maximum rotational speed and maximum torque value.

In addition, the power tool for orthopedic surgery may further include an operation trigger for operation or non-operation of the power tool.

In addition, the operation trigger may include a trigger for forward rotation and a trigger for reverse rotation, respectively, the trigger for forward rotation and the trigger for reverse rotation may each have a second magnet, and when sensing the second magnet of the trigger for forward rotation through a second magnetic sensor portion, the control portion may cause the motor to rotate in a forward direction, and when sensing the second magnet of the trigger for reverse rotation, the control portion may cause the motor to rotate in a reverse direction.

Further, the power tool body may include a trigger groove for forward rotation and a trigger groove for reverse rotation, to receive the trigger for forward rotation and the trigger for reverse rotation to be inserted therein, respectively, a spring for the trigger for forward rotation, which is inserted into the trigger groove for forward rotation in a compressed state, with one end being in contact with the trigger for forward rotation, and a spring for the trigger for reverse rotation, which is inserted into the trigger groove for reverse rotation in a compressed state, with one end being in contact with the trigger for reverse rotation.

The power tool for orthopedic surgery having the configuration described above according to embodiments has the following effects.

The power tool for orthopedic surgery can be coupled with individual attachments required for surgical operation, and also identify the coupled attachments and accordingly control the maximum rotational speed and maximum torque value of the motor, so that it is possible to improve related problems such as interruption of surgery due to inappropriate rotational speed or torque value.

In addition, the receiving portion includes the non-magnetic portion formed in the sensing direction of the first magnetic sensor, so that the first magnetic sensor senses the magnet of the attachment without being disturbed and accurately identify the individual attachments.

Meanwhile, although the present disclosure is not explicitly described, it also includes other effects that can be expected from the configuration described above.

BRIEF DESCRIPTION OF THE DRAWING

The above and other objects, features and advantages of the present disclosure will become more apparent to those of ordinary skill in the art by describing in detail exemplary embodiments thereof with reference to the accompanying drawing, in which.

DETAILED DESCRIPTION

Hereinafter, preferred embodiments of the present disclosure will be described in detail with reference to the accompanying drawings, that will be readily apparent to those skilled in the art to which the present disclosure pertains. However, the description proposed herein is just a preferable example for the purpose of illustrations only, not intended to limit the scope of the disclosure, so it should be understood that other equivalents and modifications could be made thereto without departing from the scope of the disclosure.

A power tool 100 for orthopedic surgery according to an embodiment is the power tool 100 for orthopedic surgery which can be coupled with an attachment 500 (see FIG. 7) having one or more first magnets 501 mounted thereon.

Figure 1:
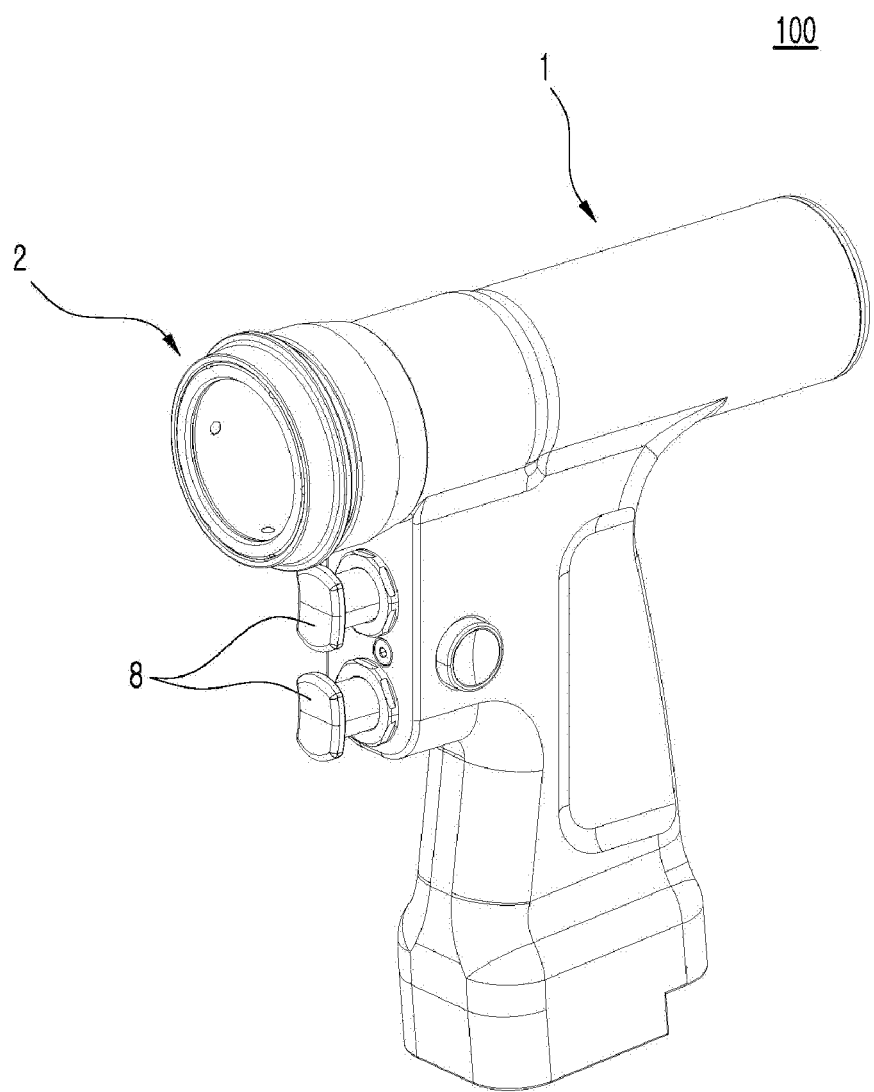
FIG. 1 is a perspective view of a power tool for orthopedic surgery according to an embodiment.
Figure 11:
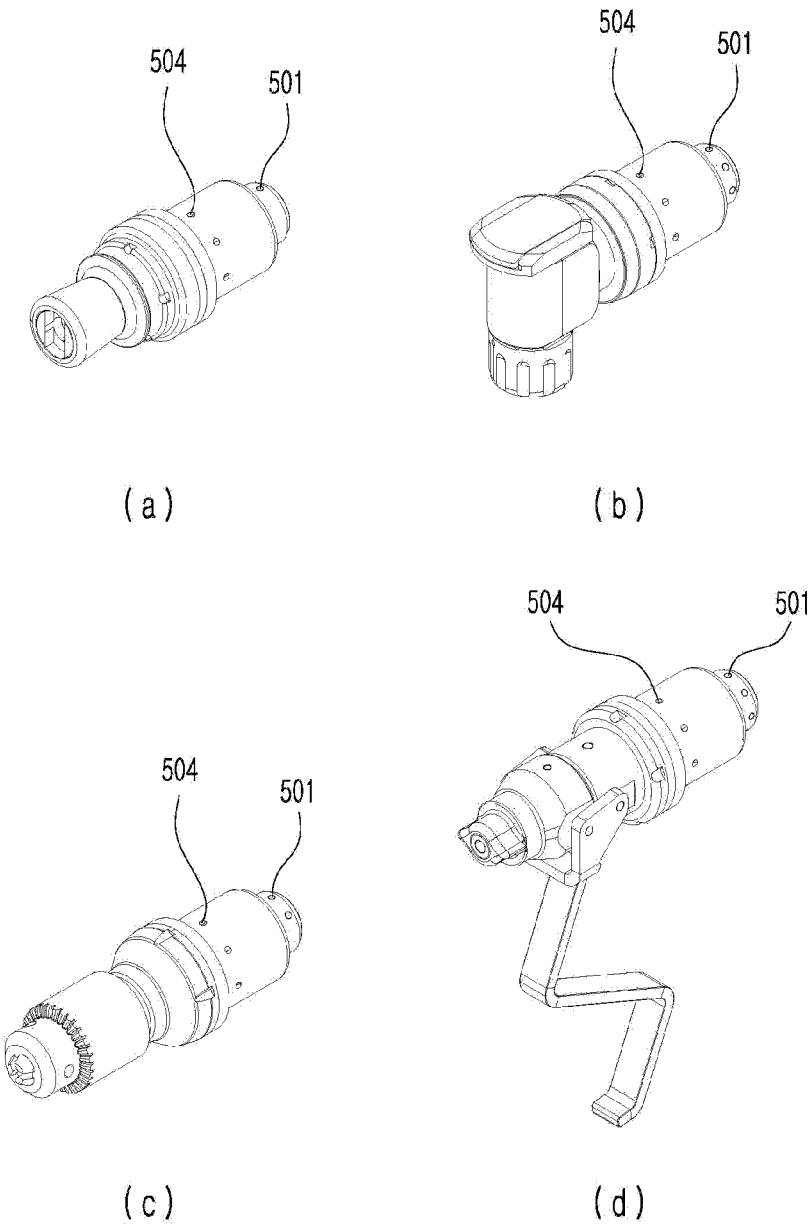
FIG. 11 illustrates attachments for various uses according to an embodiment.

As illustrated in FIG. 11, for the attachment 500, an attachment for trimming a bone and implanting a screw for bone fusion (FIG. 11A), an attachment for cutting a bone (FIG. 11B), an attachment for perforating a bone (FIG. 1C), an attachment for implanting wire pins (FIG. 11D), and the like may be used. Meanwhile, since the attachments 500 described above have the same main configuration to be described below so as to be coupled with the power tool 100 for orthopedic surgery, in this embodiment, for convenience of description, an embodiment will be exemplarily described, in which the attachment for perforating a bone (FIG. 1C) is mounted to the power tool 100 for orthopedic surgery.

As illustrated in FIGS. 1 to 4, the power tool 100 for orthopedic surgery includes, as the main components, a power tool body 1, an attachment fastening portion 2, a motor power transmitting portion 3, a motor 4, a first magnetic sensor portion 5, a control portion 6, and a power supply.

The power tool body 1 includes a power tool case 11.

The attachment fastening portion 2 is connected to one end (the front portion, on the left side based on FIG. 3) of the power tool body 1. In addition, the attachment fastening portion 2 includes a receiving portion 21 for receiving the attachment 500.

In addition, the attachment fastening portion 2 further includes a sliding portion 22 slidable relative to the receiving portion 21.

Figure 4:
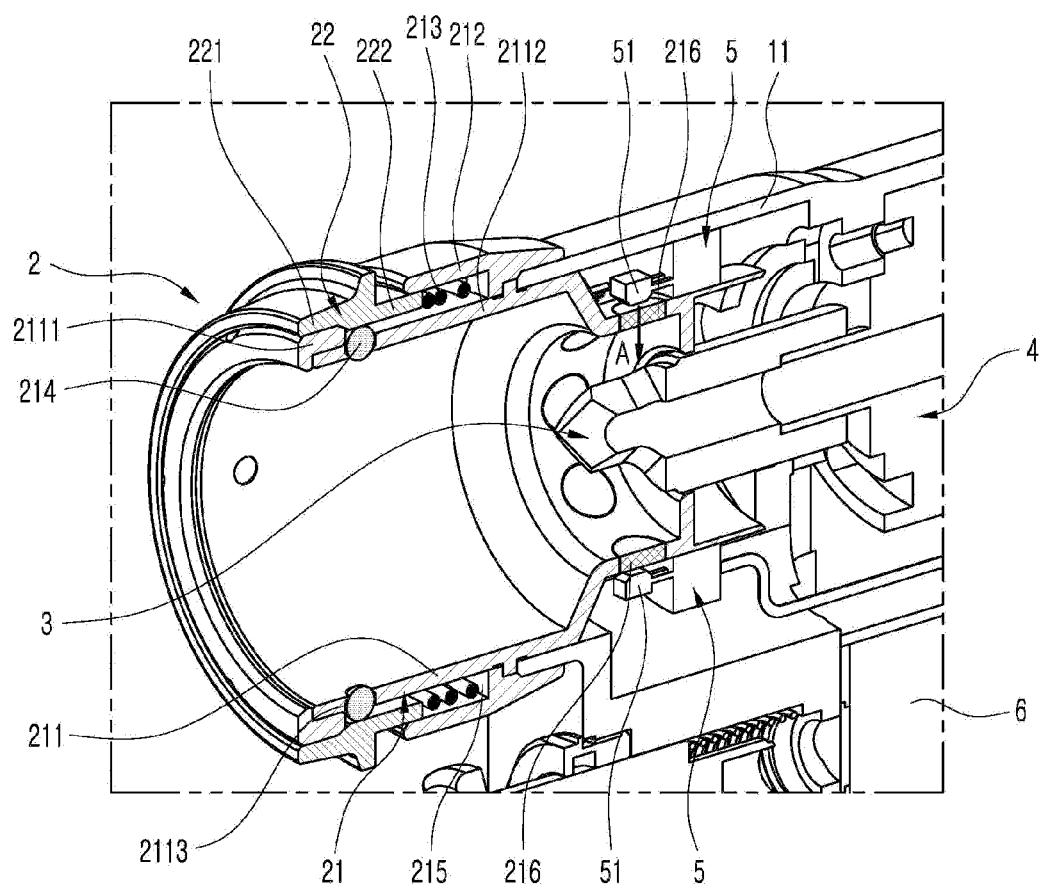
FIG. 4 is a perspective cross-sectional view of the main configuration of the power tool of FIG. 1.
Figure 5:
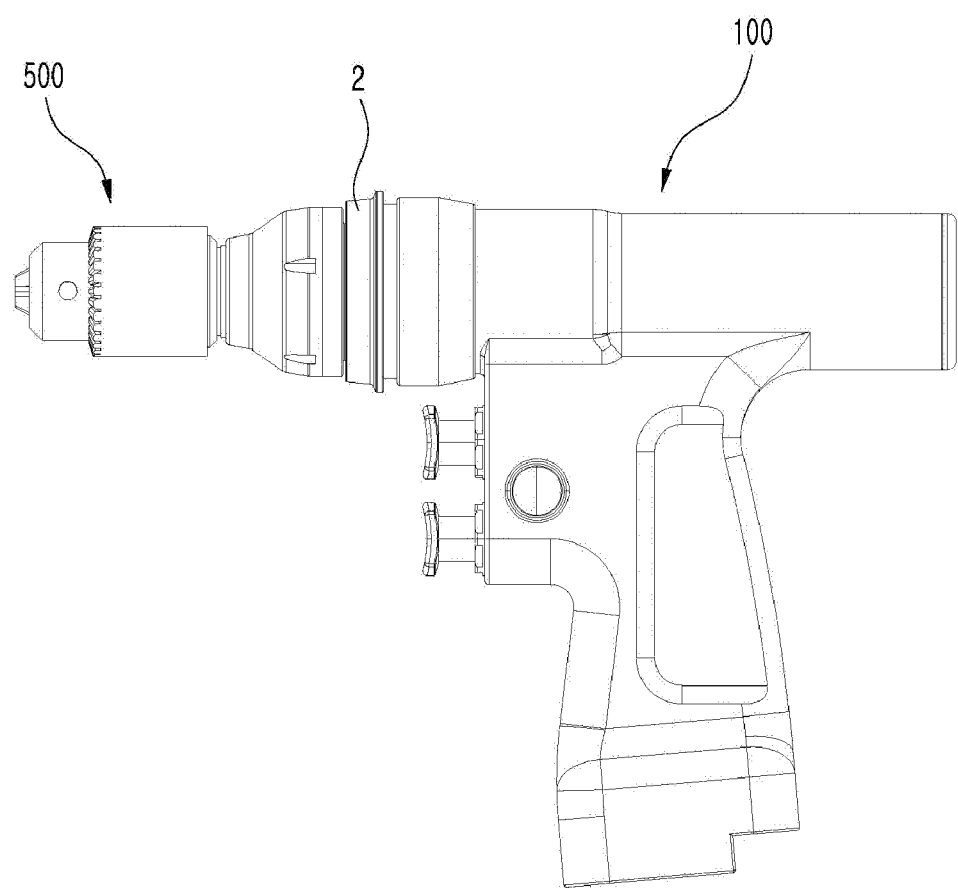
FIG. 5 illustrates the attachment according to an embodiment mounted on the power tool of FIG. 1.
Figure 6:
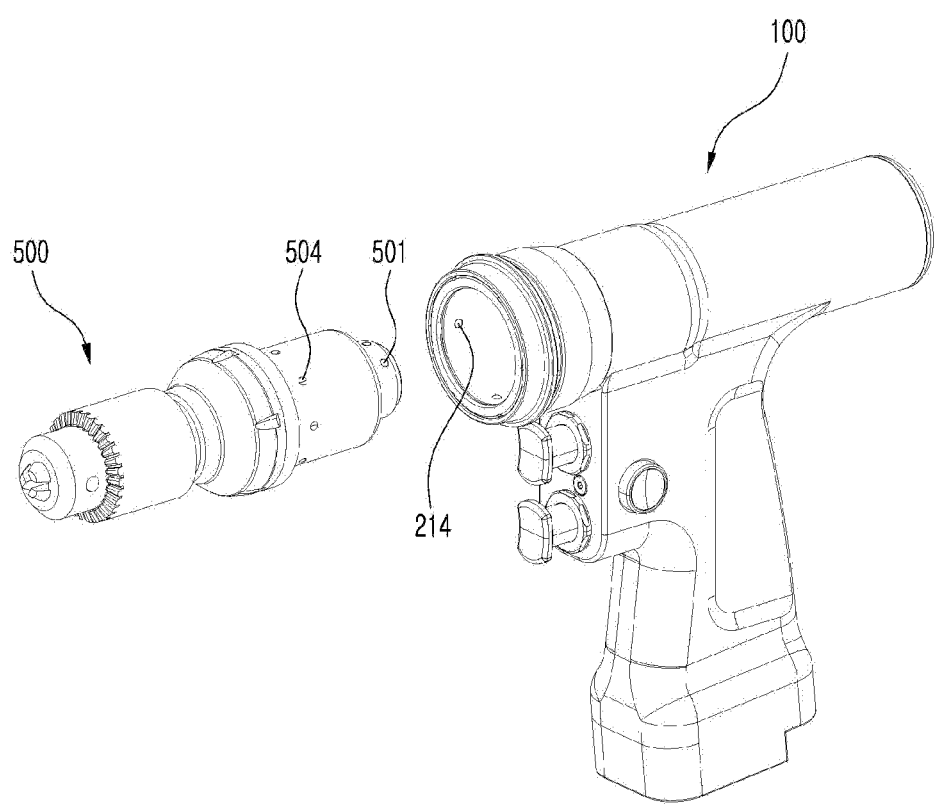
FIG. 6 illustrates the attachment of FIG. 5 is separated from the power tool of FIG. 1.

The sliding portion 22 has a substantially cylindrical shape and includes a sliding portion distal end 221 and a sliding portion proximal end 222 having an inner diameter smaller than that of the sliding portion distal end 221 (see FIG. 4).

As illustrated in FIG. 4, the receiving portion 21 includes a non-magnetic portion 216 formed in a sensing direction A of a first magnetic sensor 51 to be described below. For reference, as is well known, the magnetic sensor is a sensor that can measure the magnitude of a magnetic field or the magnitude and direction of a magnetic field line, in which the magnetic field is a vector physical quantity having a direction. Accordingly, the non-magnetic portion 216 formed of a non-magnetic material instead of a magnetic material is provided in the sensing direction A of the first magnetic sensor 51, so that the first magnetic sensor 51 can sense the magnets 501 of the attachment 500 without being disturbed.

In addition, the receiving portion 21 includes an inner member 211, an outer member 212, a first elastic member 213, and a plurality of fastening balls 214 (see FIG. 4).

Specifically, the inner member 211 receives the attachment 500 therein, and it includes an inner member distal end 2111 and an inner member proximal end 2112 having an outer diameter smaller than the inner member distal end 2111.

The outer member 212 forms an annular groove 215 in cooperation with the inner member proximal end 2112.

The first elastic member 213 is disposed in a compressed state in the annular groove 215, with one end disposed in contact with the sliding portion 22.

The plurality of fastening balls 214 are positioned in a circumferential direction of the inner member 211, are respectively disposed in the plurality of through holes 2113 in the wall thickness direction of the inner member 211, and moved in a wall thickness direction of the inner member 211.

The motor power transmitting portion 3 protrudes from the inside of the receiving portion 21 toward the attachment fastening portion 2, and transmits the power received from the motor 4 to the attachment 500.

The motor 4 drives (rotates) the motor power transmitting portion 3.

Figure 2:
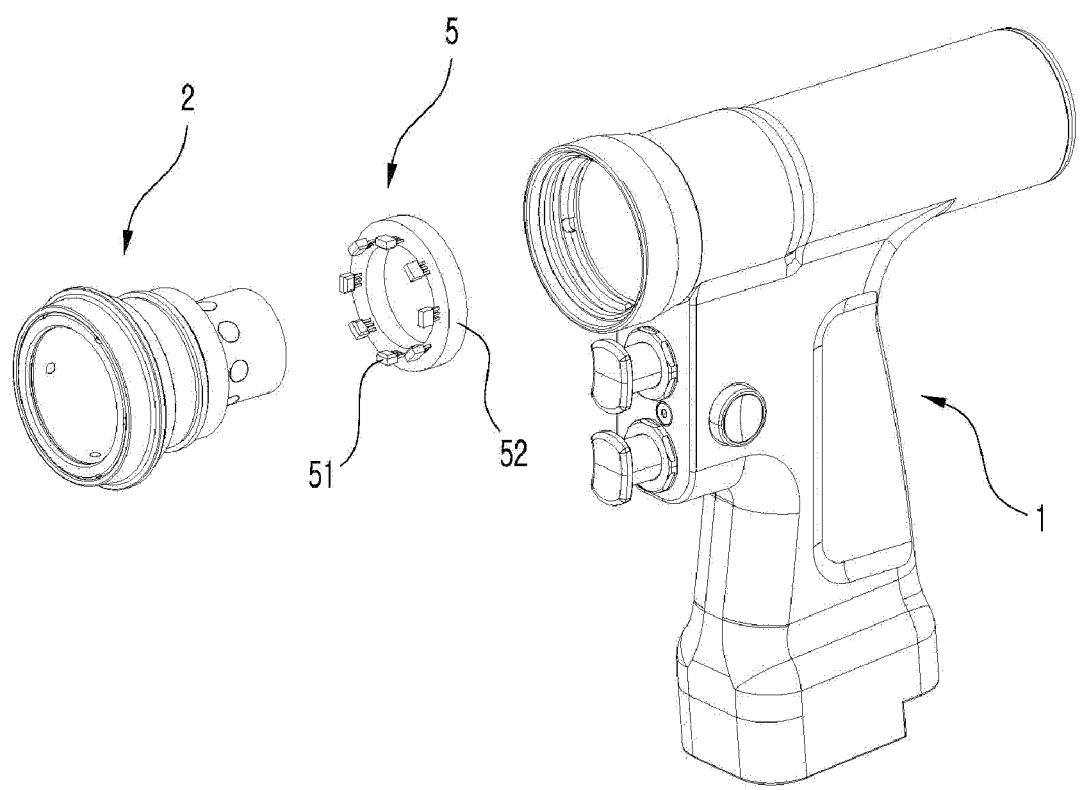
FIG. 2 is an exploded view of a main configuration of the power tool of FIG. 1.
Figure 3:
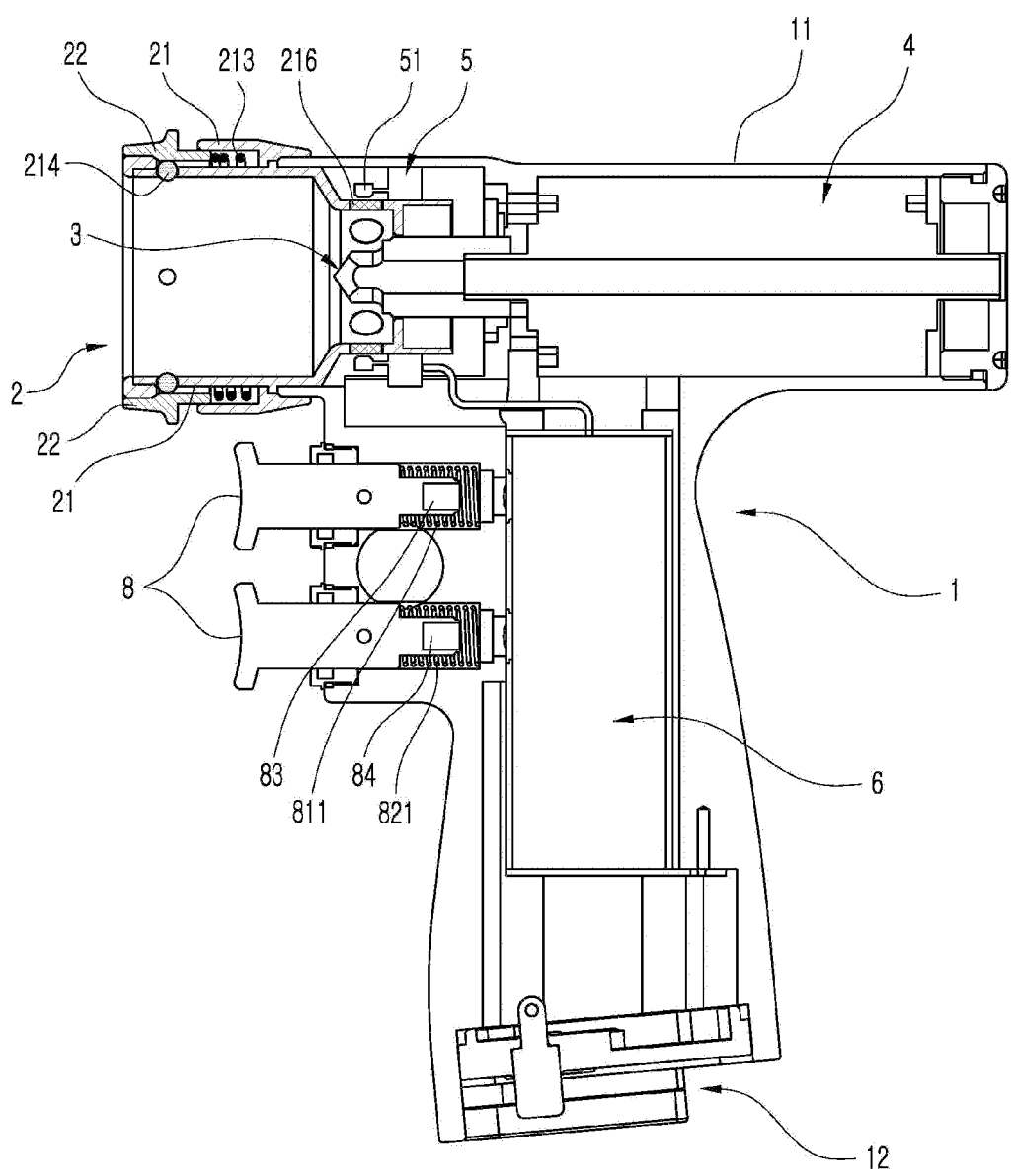
FIG. 3 is a cross-sectional view of the power tool of FIG. 1.

The first magnetic sensor portion 5 includes the first magnetic sensor 51 capable of sensing the magnetic field strength or number of the one or more first magnets 501 mounted on the attachment 500. As illustrated in FIG. 2, the first magnetic sensor portion 5 includes a plurality of first magnetic sensors 51 disposed on an annular ring portion 52 at predetermined intervals in the circumferential direction. In this embodiment, for example, the first magnetic sensor portion 5 includes eight first magnetic sensors 51.

Meanwhile, for the first magnets 501 of the attachment 500, at least one first magnet is disposed on the attachment 500 at a position corresponding to the position of the first magnetic sensor 51.

Referring to FIG. 11, by way of example, one first magnet is disposed on the attachment for trimming a bone and implanting a screw for bone fusion (FIG. 11A), three first magnets are disposed on the attachment for cutting a bone (FIG. 11B), two first magnets are disposed on the attachment for perforating a bone (FIG. 1C), and four first magnets are disposed on the attachment for implanting wire pins (FIG. 11D).

In addition, the first magnetic sensor portion 5 is electrically connected to the control portion 6.

Further, as illustrated in FIG. 4, the first magnetic sensor portion 5 is disposed between the outer wall of the receiving portion 21 and the inner wall of the power tool case 11.

The control portion 6 controls the motor 4 below a preset maximum rotational speed (rpm) and maximum torque value (N cm) according to the strength or number of the magnetic fields sensed by the first magnetic sensor 51.

Figure 12:
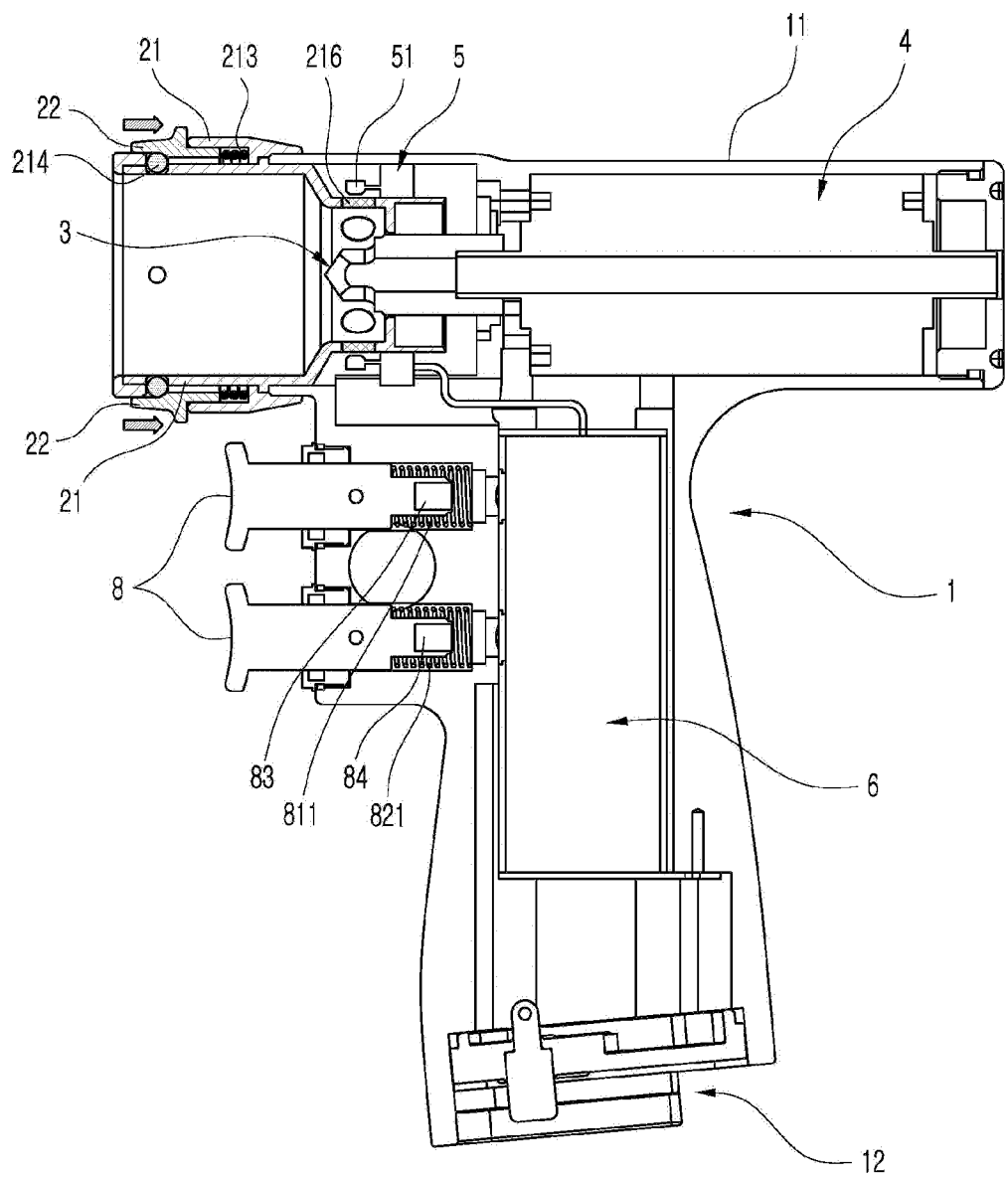
FIG. 12 illustrates a sliding portion moved rearward to couple the attachment of FIG. 5 to the power tool of FIG. 1.

A power supply (not illustrated) may be mounted on a power connection unit 12 located at a lower end of the power tool body 1, and may supply required power to the motor 4 and the control portion 6 (see FIG. 12). For example, the power supply may be a portable and replaceable battery.

Figure 7A:
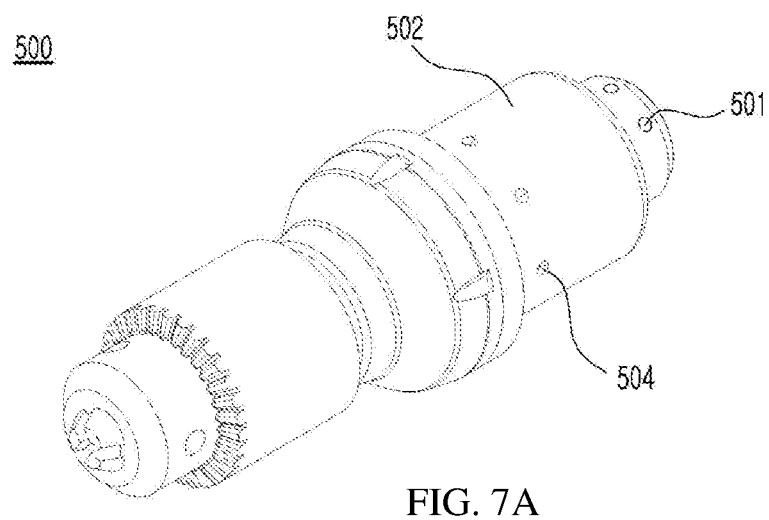
FIGS. 7A and 7B show a rear perspective view and a front perspective view of the attachment of FIG. 5.
Figure 7B:
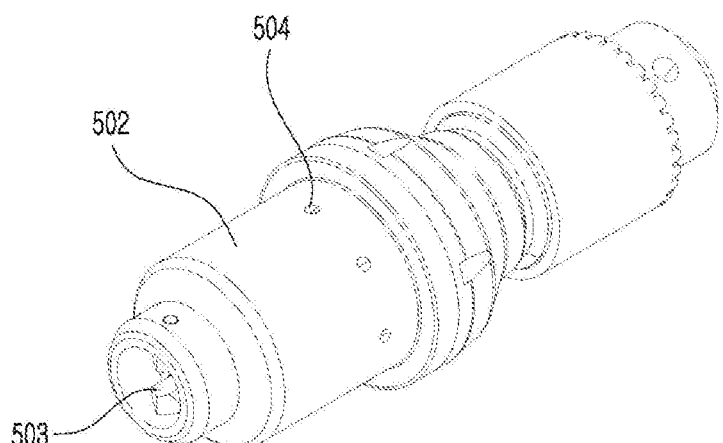
Figure 8:
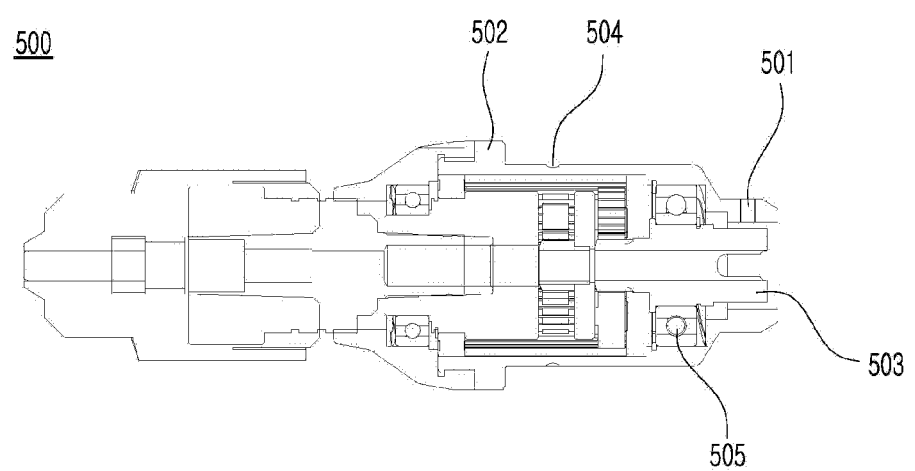
FIG. 8 is a cross-sectional view of the attachment of FIG. 5.

Meanwhile, as illustrated in FIGS. 7 and 8, the attachment 500 includes an attachment body 502 and a power transmission fastening portion 503 as main components. For reference, in this embodiment, in relation to the attachment 500, the main configuration for fastening with the present power tool will be described, and the description of the already known configuration, for example, the reduction gear fastened to the power transmission fastening portion 503 and the like, which is irrelevant to the gist of the present disclosure, will be omitted.

Figure 9:
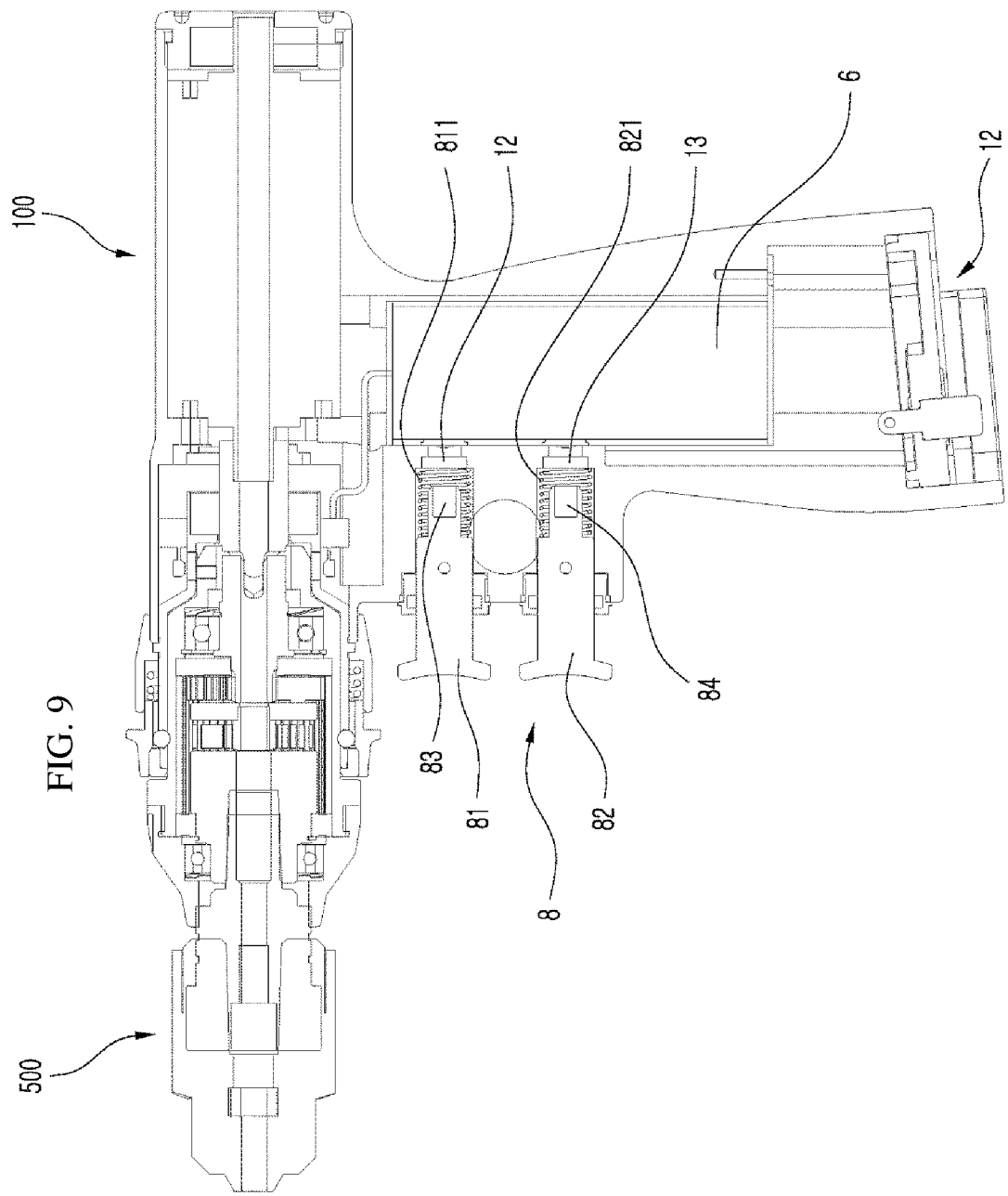
FIG. 9 is a cross-sectional view of the attachment and the power tool of FIG. 5 coupled with each other.
Figure 10:
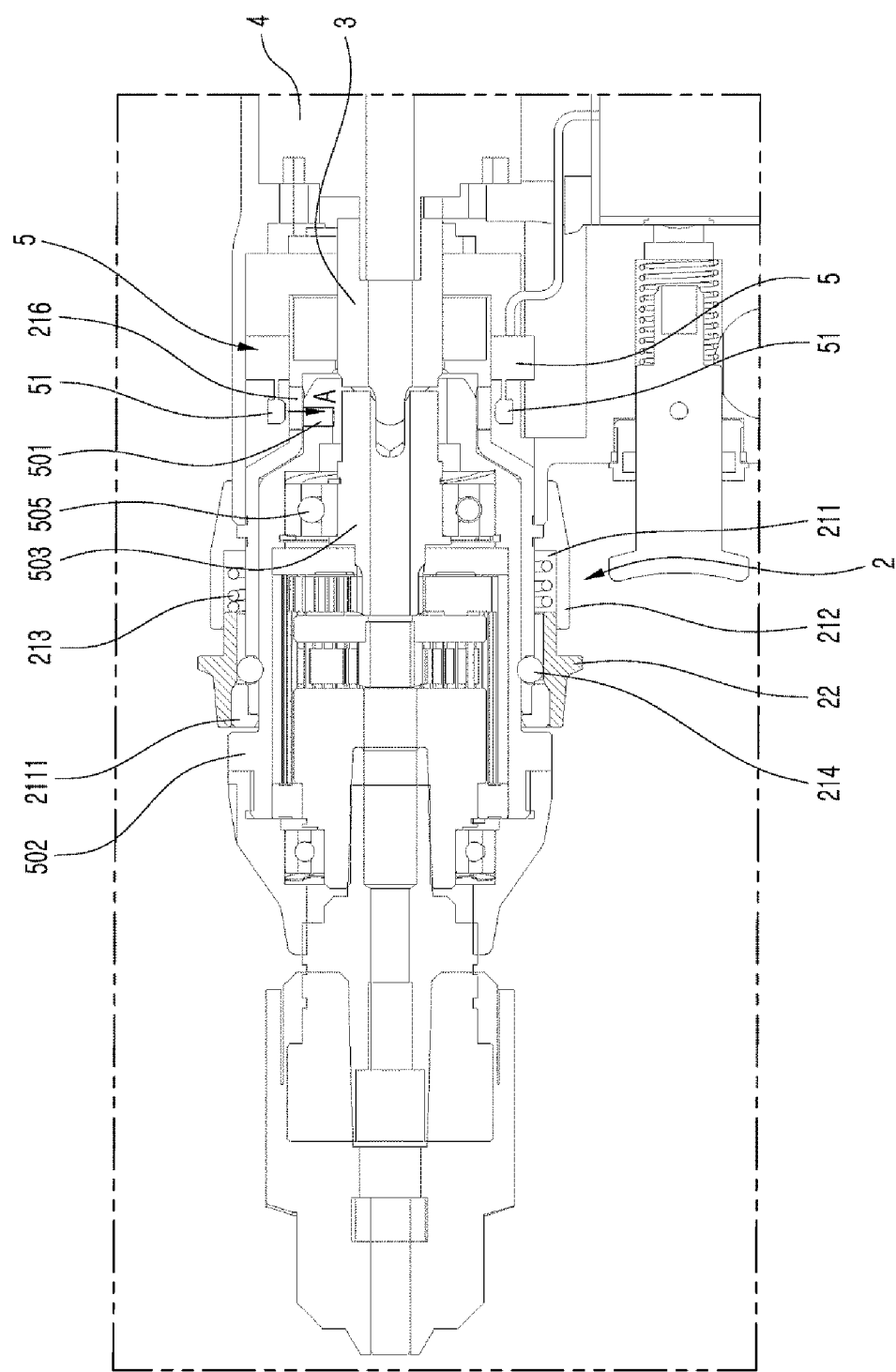
FIG. 10 is an enlarged cross-sectional view of the main portion of FIG. 9.

As illustrated in FIGS. 8 to 10, the attachment body 502 is received in the receiving portion 21.

The power transmission fastening portion 503 is disposed inside the attachment body 502, and is coupled with the motor power transmitting portion 3 of the power tool 100 so as to be rotatable relative to the attachment body 502 while interlocking with the motor power transmitting portion 3. To this end, a bearing 505 may be mounted between the attachment body 502 and the power transmission fastening portion 503.

Meanwhile, the one or more first magnets 501 are provided on the attachment body 502 in the circumferential direction, and disposed to face the first magnetic sensor 51 while the non-magnetic portion 216 of the receiving portion 21 is interposed between itself and the first magnetic sensor 51.

In addition, an attachment body 500 includes a plurality of fastening ball grooves 504 at positions corresponding to the positions of the plurality of fastening balls 214.

When the attachment body 500 is completely received in the inner member 211 of the power tool 100 such that the power transmission fastening portion 503 is coupled with the motor power transmitting portion 3 of the power tool 100, a portion of the fastening ball 214 of the power tool 100 is inserted into the fastening ball groove 504, and the attachment body 500 is fixed to the inner member 211.

In addition, when the sliding portion 22 is slid from the inner member distal end 2111 toward the inner member proximal end 2112 while overcoming the restoring force of the first elastic member 213, the fastening ball 214 may be separated from the fastening ball groove 504 while moving toward the sliding portion distal end 221, and the attachment body 500 may be relatively moved while being released from being fixed to the inner member 211.

When there is one first magnet 501 mounted on the attachment 500, the control portion 6 senses what kind of attachment 500 is mounted according to the strength of the magnetic field sensed by the first magnetic sensor 51 and control the motor 4 so as not to exceed a preset maximum rotational speed and maximum torque value. That is, when one first magnet 501 is mounted on the attachment 500, the first magnets having different magnetic field strengths are used for each of the attachments 500.

When two or more first magnets 501 are mounted on the attachment 500, according to the number of first magnets

501 sensed by the first magnetic sensor 51, the control portion 6 controls the motor 4 so as not to exceed the preset maximum rotational speed and maximum torque value. In this case, the first magnets having the same magnetic field strength are used.

In other words, when one first magnet is mounted, the strength of the magnetic field may be sensed, and when a plurality of first magnets are mounted, the number of magnets may be sensed, to recognize which attachments are fastened and control the voltage and current values of the motor so that the motor remains below the preset maximum rotational speed and maximum torque value. Since the maximum rotational speed and maximum torque value suitable for a specific surgical operation can be easily ensured mechanically, it is possible to improve the related problems caused by relying on the user's experience.

As illustrated in FIG. 9, the power tool 100 for orthopedic surgery may further include an operation trigger 8 for operation or non-operation of the motor 4.

Specifically, the operation trigger 8 includes a trigger 81 for forward rotation and a trigger 82 for reverse rotation, respectively. In addition, the trigger 81 for forward rotation and the trigger 82 for reverse rotation include second magnets 83 and 84, respectively.

When sensing the second magnet 83 of the trigger 81 for forward rotation through the second magnetic sensor portion (not illustrated), the control portion 6 causes the motor 4 to rotate in a forward direction, and when sensing the second magnet 84 of the trigger 82 for reverse rotation, the control portion 6 causes the motor 4 to rotate in a reverse direction. For example, by adjusting the strength of the magnetic field sensed by the second magnetic sensor portion according to a distance between the second magnet and the second magnetic sensor portion, it is possible to adjust the rotational speed and torque value of the motor.

Meanwhile, the power tool body 1 includes a trigger groove 12 for forward rotation and a trigger groove 13 for reverse rotation, to receive the trigger 81 for forward rotation and the trigger 82 for reverse rotation to be inserted therein, respectively, a spring 811 for the trigger for forward rotation, which is inserted into the trigger groove 12 for forward rotation in a compressed state, with one end being in contact with the trigger 81 for forward rotation, and a spring 821 for the trigger for reverse rotation, which is inserted into the trigger groove 13 for reverse rotation in a compressed state, with one end being in contact with the trigger 82 for reverse rotation.

Hereinafter, with reference to FIGS. 9, 12, and 13, the operation of the power tool for orthopedic surgery having the configuration described above according to an embodiment will be described.

User selects the attachment 500 required for a particular surgical task. In this embodiment, the attachment 500 for perforating a bone will be described as an example.

As illustrated in FIG. 12, in order to couple the attachment 500 to the power tool 100, the sliding portion 22 is moved rearward relative to the receiving portion 21. At this time, the fastening ball 214 is moved toward the sliding portion distal end 221 having a relatively larger inner diameter so as to avoid interference when the attachment 500 is inserted into the receiving portion 21.

Figure 13:
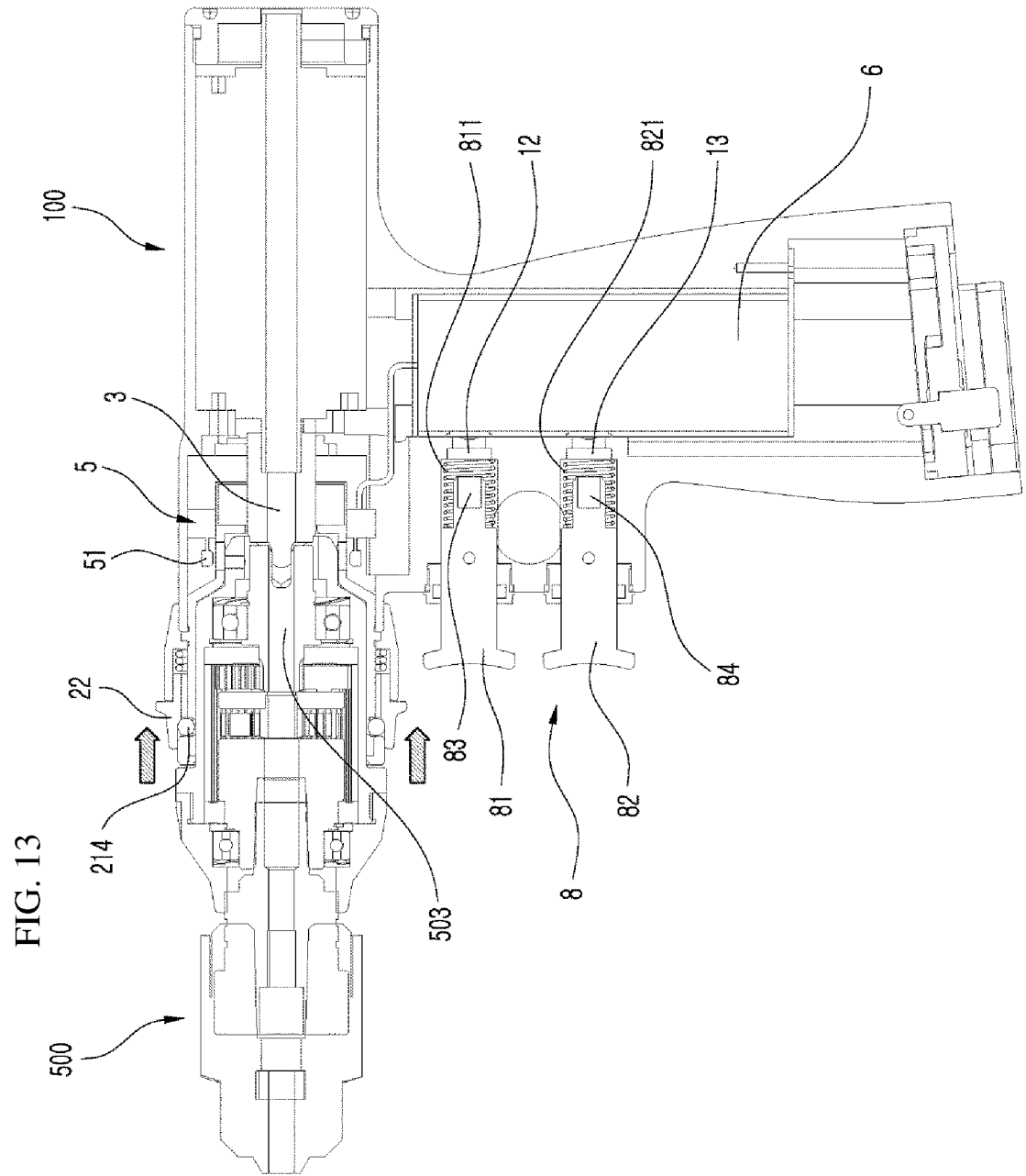
FIG. 13 illustrates, in the state of FIG. 12, the attachment inserted in the power tool of FIG. 1.

Next, the attachment 500 is inserted into the receiving portion 21 so that the power transmission fastening portion 503 of the attachment 500 is coupled with the motor power transmitting portion 3 of the power tool 100 (see FIG. 13).

Next, as illustrated in FIG. 9, when the force applied to the sliding portion 22 is removed, the sliding portion 22 is moved forward relative to the receiving portion 21 by the restoring force of the first elastic member 213. At this time, as the fastening ball 214 is brought into contact with the sliding portion proximal end 222, with its portion protruding into the inside of the receiving portion 21, the fastening ball 214 is coupled with the fastening ball groove 504 of the attachment 500. Accordingly, the attachment 500 is fixed and limited in its movement relative to the power tool 100.

At this time, the first magnetic sensor portion 5 of the power tool 100 senses that the number of the first magnets 501 is two, and transmits the information to the control portion 6. For reference, as described above, on every attachment 500, there may be disposed only one first magnet of different magnetic field strength. Then, the first magnetic sensor portion 5 may also recognize the type of the mounted attachment according to the strength of the sensed magnetic field.

Then, as the user is enabled to perform surgery while the control portion 6 controls the recognized attachment 500 to operate below the preset maximum rotational speed and maximum torque value, it is possible to prevent problems such as bone necrosis and the like caused by high heat due to an excessively high rotational speed that may occur when using a related power tool for surgery.

The present disclosure has been described in detail. However, it should be understood that the detailed description and specific examples, while indicating preferred embodiments of the disclosure, are given by way of illustration only, since various changes and modifications within the scope of the disclosure will become apparent to those skilled in the art from this detailed description.

What is claimed is:

1. A power tool for orthopedic surgery which can be coupled with an attachment having one or more first magnets mounted thereon, the power tool comprising:
    a power tool body including a power tool case;
    an attachment fastening portion connected to one end of the power tool body;
    a motor power transmitting portion protruding toward the attachment fastening portion and transmitting power to the attachment;
    a motor that drives the motor power transmitting portion;
    a first magnetic sensor portion including a first magnetic sensor capable of sensing a magnetic field strength or number of the one or more first magnets;
    a control portion that controls the motor to operate below a preset maximum rotational speed and maximum torque value according to the magnetic field strength or the number sensed by the first magnetic sensor; and
    a power supply that supplies power to the motor and the control portion,
    wherein the attachment fastening portion includes a receiving portion for receiving the attachment,
    the first magnetic sensor portion is disposed between an outer wall of the receiving portion and the power tool case, and
    the receiving portion includes a non-magnetic portion formed in a sensing direction of the first magnetic sensor.

2. An assembly comprising:
    the power tool for orthopedic surgery according to claim 1; and
    the attachment to which the power tool can be coupled and having one or more first magnets mounted thereon,
    wherein the attachment includes:
        an attachment body to be received in the receiving portion; and a power transmission fastening portion disposed inside the attachment body and rotatable relative to the attachment body while interlocking with the motor power transmitting portion, and wherein the one or more first magnets are provided on the attachment body in a circumferential direction, and are disposed to face the first magnetic sensor while the nonmagnetic portion of the receiving portion is interposed between itself and the first magnetic sensor.

3. The assembly according to claim 2, wherein the attachment fastening portion further includes a sliding portion slidable relative to the receiving portion, the sliding portion includes a sliding portion distal end and a sliding portion proximal end having an inner diameter smaller than the sliding portion distal end, and the receiving portion includes:
an inner member receiving the attachment therein and including an inner member distal end and an inner member proximal end having an outer diameter smaller than the inner member distal end;
an outer member forming an annular groove in cooperation with the inner member proximal end;
a first elastic member disposed in the annular groove in a compressed state, with one end disposed in contact with the sliding portion; and
a plurality of fastening balls respectively disposed in a plurality of through holes in a wall thickness direction of the inner member and movable in the wall thickness direction of the inner member.

4. The assembly according to claim 3, wherein the attachment body includes a plurality of fastening ball grooves at positions corresponding to positions of the plurality of fastening balls, and when the attachment body is completely received in the inner member such that the power transmission fastening portion is coupled with the motor power transmitting portion, a portion of each of the plurality of fastening balls is inserted into a corresponding one of the plurality of fastening ball grooves such that the attachment body is fixed to the inner member, and when the sliding portion is slid from the inner member distal end toward the inner member proximal end while overcoming a restoring force of the first elastic member, each of the plurality of fastening balls is separated from the corresponding one of the plurality of fastening ball grooves while moving toward the sliding portion distal end such that the attachment body may be released from being fixed to the inner member.

5. The power tool for orthopedic surgery according to claim 1, wherein the first magnetic sensor portion is electrically connected to the control portion.

6. The power tool for orthopedic surgery according to claim 1, wherein, when one first magnet is mounted on the attachment, according to a magnetic field strength sensed by the first magnetic sensor, the control portion controls the motor to operate below the preset maximum rotational speed and maximum torque value, and when two or more first magnets are mounted on the attachment, according to the number of the one or more first magnets sensed by the first magnetic sensor, the control portion controls the motor to operate below the preset maximum rotational speed and maximum torque value.

7. The power tool for orthopedic surgery according to claim 6, wherein the power tool for orthopedic surgery further includes an operation trigger for operation or non-operation of the motor.

8. The power tool for orthopedic surgery according to claim 7, wherein the operation trigger includes a trigger for forward rotation and a trigger for reverse rotation, respectively, and the trigger for forward rotation and the trigger for reverse rotation each have a second magnet, wherein, when sensing the second magnet of the trigger for forward rotation through a second magnetic sensor portion, the control portion causes the motor to rotate in a forward direction, and when sensing the second magnet of the trigger for reverse rotation, the control portion causes the motor to rotate in a reverse direction.

9. The power tool for orthopedic surgery according to claim 8, wherein the power tool body includes:
a trigger groove for forward rotation and a trigger groove for reverse rotation, to receive the trigger for forward rotation and the trigger for reverse rotation to be inserted therein, respectively;
a spring for the trigger for forward rotation, which is inserted into the trigger groove for forward rotation in a compressed state, with one end being in contact with the trigger for forward rotation; and
a spring for the trigger for reverse rotation, which is inserted into the trigger groove for reverse rotation in a compressed state, with one end being in contact with the trigger for reverse rotation.

* * * * *